United States Patent
Boettcher

(10) Patent No.: US 10,634,755 B2
(45) Date of Patent: Apr. 28, 2020

(54) METHOD AND APPARATUS FOR GENERATING CORRECTED MAGNETIC RESONANCE MEASUREMENT DATA

(71) Applicant: Siemens Healthcare GmbH, Erlangen (DE)

(72) Inventor: Uwe Boettcher, Uttenreuth (DE)

(73) Assignee: Siemens Healthcare GmbH, Erlangen (DE)

(*) Notice: Subject to any disclaimer, the term of this patent is extended or adjusted under 35 U.S.C. 154(b) by 175 days.

(21) Appl. No.: 15/850,556

(22) Filed: Dec. 21, 2017

(65) Prior Publication Data
US 2018/0172791 A1 Jun. 21, 2018

(30) Foreign Application Priority Data
Dec. 21, 2016 (DE) .................. 10 2016 225 705

(51) Int. Cl.
*G01R 33/565* (2006.01)
*A61B 5/055* (2006.01)

(52) U.S. Cl.
CPC ........ *G01R 33/56527* (2013.01); *A61B 5/055* (2013.01); *G01R 33/56563* (2013.01)

(58) Field of Classification Search
CPC ........ G01R 33/56527; G01R 33/56563; A61B 5/055
See application file for complete search history.

(56) References Cited

U.S. PATENT DOCUMENTS

| | | | |
|---|---|---|---|
| 8,498,688 B2* | 7/2013 | Lamerichs | G01R 33/485 600/407 |
| 9,615,768 B2* | 4/2017 | Nishihara | A61B 5/055 |
| 2002/0145424 A1 | 10/2002 | Uetake | |
| 2005/0248343 A1 | 11/2005 | Kruger et al. | |
| 2012/0235683 A1 | 9/2012 | Weiland | |
| 2014/0300357 A1* | 10/2014 | Bachschmidt | G01R 33/56536 324/309 |

FOREIGN PATENT DOCUMENTS

DE 102005015069 A1 10/2006

* cited by examiner

*Primary Examiner* — Patrick Assouad
*Assistant Examiner* — Feba Pothen
(74) *Attorney, Agent, or Firm* — Schiff Hardin LLP

(57) ABSTRACT

In a method and apparatus for generating corrected magnetic resonance measurement data in an examination region of an object undergoing examination, a magnetic resonance sequence is applied to a subject in order to acquire magnetic resonance measurement data from an examination region within a time period. A first resonant frequency of nuclear spins in the examination region is determined at a first time point within the time period. A second resonant frequency of nuclear spins in the examination region is determined at a second time point within the time period. Magnetic resonance measurement data that are acquired at a further time point within the time period are corrected, based on the first resonant frequency and the second resonant frequency.

18 Claims, 2 Drawing Sheets

US 10,634,755 B2

METHOD AND APPARATUS FOR GENERATING CORRECTED MAGNETIC RESONANCE MEASUREMENT DATA

BACKGROUND OF THE INVENTION

Field of the Invention

The invention concerns a method, a magnetic resonance apparatus, an electronically readable data storage medium encoded with programming instructions, for generating corrected magnetic resonance measurement data in an examination region of an object undergoing examination.

Description of the Prior Art

In magnetic resonance examinations, using a magnetic resonance scanner, the body that is to be investigated of a person undergoing examination, in particular a patient, is exposed to a relatively strong basic magnetic field, for example of 1.5 or 3 or 7 tesla, by operation of a basic field magnet. In addition, a gradient coil arrangement is used to apply gradient magnetic fields. A suitable radio-frequency antenna is then used to emit radio-frequency pulses, for example excitation pulses, that result in nuclear spin in certain atoms being are excited to resonance, and being tipped by a defined flip angle in relation to the magnetic field lines of the basic magnetic field. On relaxation of the nuclear spins, radio-frequency signals, so-called magnetic resonance signals, are emitted and these are received using suitable radio-frequency antennas, and then undergo further processing. This allows magnetic resonance measurement data to be acquired in a defined region of the object undergoing examination, the examination region. Thus, for a particular measurement it is necessary to emit a specific magnetic resonance sequence that includes a series of radio-frequency pulses, for example excitation pulses and refocusing pulses, and gradient fields activated in a coordinated manner, on different gradient axes in different spatial directions. Readout windows are accordingly defined in relation to time that predetermine the periods during which the induced magnetic resonance signals, the magnetic resonance measurement data, are acquired.

The frequency of the radio-frequency pulses, that is to say the frequency at which the radio-frequency pulses are actually applied in the object by the radio-frequency antenna unit, is designated the emission frequency or the carrier frequency. The frequency of the nuclear spins, the resonant frequency, is defined by the strength of the basic magnetic field, and corresponds to the Larmor frequency of the nuclear spins in relation to the strength of the basic magnetic field. During the application of a magnetic resonance sequence, in order to capture magnetic resonance measurement data, typically a match between the carrier frequency and the resonant frequency, or a defined relationship between the two frequencies, is desirable. During the application of a magnetic resonance sequence, the resonant frequency may vary, such as because of external influences, which can affect the magnetic resonance measurement data to be acquired. Such external influences may change (vary) the strength of the basic magnetic field, with the result that the Larmor frequency can be changed. Typically, this is not desirable, so it may be necessary to stabilize the resonant frequency or to correct the magnetic resonance measurement data.

DE 102005015069 A1 describes a method for avoiding linear phase errors using an adjustment of the resonant frequency of the nuclear spins. DE 102011005614 B3 describes a method for detecting fault signals in magnetic resonance spectroscopy.

SUMMARY OF THE INVENTION

An object of the invention is to provide a simple and precise method for generating corrected magnetic resonance measurement data in an examination region of an object undergoing examination.

The method according to the invention for generating corrected magnetic resonance measurement data in an examination region of an object undergoing examination includes the following steps.

A magnetic resonance data acquisition scanner is operated in order to apply a magnetic resonance sequence to an examination region of a subject, for acquiring magnetic resonance measurement data within a time period.

A computer that operates the scanner determines a first resonant frequency of nuclear spins in the examination region of the subject at a first time point within the time period.

The computer determines a second resonant frequency of the nuclear spins in the examination region at a second time point within the time period.

The computer corrects magnetic resonance measurement data that are acquired at a further time point within the time period, based on the first resonant frequency and the second resonant frequency.

The time period preferably specifies a length of time during which the magnetic resonance sequence is actually applied. The time period includes the first time point and the second time point. The first time point may be representative of a first time range of the time period. The second time point may be representative of a second time range of the time period. The first time range and the second time range are different from one another to at least a certain extent, preferably being separated from one another. The first time range, for example, may specify a duration during which the raw data space, (k-space) is completely scanned (filled). Likewise, during the second time range the raw data space (k-space) may undergo complete scanning.

The first resonant frequency specifies the frequency of the radio-frequency pulses at the first time point. If the first time point represents the first time range, then the first resonant frequency is preferably representative of the Larmor frequency of nuclear spins during the first time range. The second resonant frequency preferably specifies the frequency of the radio-frequency pulses at the second time point. If the second time point represents the second time range, then the second resonant frequency is preferably representative of the Larmor frequency of nuclear spins during the second time range. The first time point, for example, may be at the start of the time period. The second time point may for example be at the end of the time period. The method may also include determination of a third resonant frequency at which the magnetic resonance sequence is applied at a third time point within the time period.

The first resonant frequency and/or the second resonant frequency may for example by determined by means of a sensor.

It is possible for magnetic resonance measurement data to be captured at the first time point and/or the second time point and to be used to determine the first resonant frequency and/or the second resonant frequency. Magnetic resonance measurement data of this kind may be generated by a module of the magnetic resonance sequence that is provided specifically for this purpose. The first resonant frequency and/or the second resonant frequency may also be extracted from magnetic resonance measurement data that were acquired at the first time point and/or the second time point and/or in the first time range and/or the second time range and is used for a diagnosis and/or assessment of the examination region of the object undergoing examination.

Correction is preferably performed such that an effect on the magnetic resonance measurement data brought about by a change in a resonant frequency is canceled out in the corrected magnetic resonance measurement data. The further time point is taken into account in the correction. Preferably, the correction includes a correction of the effect on the acquired magnetic resonance measurement data brought about by a change in the resonant frequency.

An advantage of the method according to the invention is that a change in the resonant frequency within the time period can be detected and the effect thereof on the magnetic resonance measurement data can be reduced and/or eliminated. In the case of magnetic resonance measurement data that are phase-sensitive, that is to say is acquired by a phase-sensitive magnetic resonance sequence, this is particularly advantageous. Phase-sensitive magnetic resonance sequences utilize the fact that different types of tissue have different resonant frequencies; for example, there is a chemical shift between fatty tissue and water. Thus, using a phase-sensitive magnetic resonance sequence, it is possible for example to suppress magnetic resonance signals coming from fatty tissue and/or to generate specific contrasts, for example by the Dixon method.

Phase-sensitive magnetic resonance measurement data are characterized by, instead of and/or in addition to the magnitudes of the magnetic resonance signals, the data also include the phases of the magnetic resonance signals. Typically, phase-sensitive magnetic resonance measurement data are complex-valued measurement data. Phase-sensitive magnetic resonance measurement data is typically used in spectroscopic MR imaging. Phase-sensitive magnetic resonance measurement data and/or phase-sensitive magnetic resonance sequences typically require a constant resonant frequency over the time period. External influences such as warming of the magnetic resonance device during the time period can change the resonant frequency. Warming of the magnetic resonance device during the time period may be caused by the magnetic resonance sequence itself within the time period, for example as a result of gradient switching. It is likewise conceivable for use of the magnetic resonance device before the start of the time period to have the effect of delayed warming of the magnetic resonance device during the time period.

The method according to the invention makes it possible to correct the magnetic resonance measurement data such that the corrected magnetic resonance measurement data are not affected by a change in the resonant frequency of the magnetic resonance sequence. In this context, a correction to magnetic resonance measurement data that are captured at a further time point within the time period may be made on the basis of the first resonant frequency and the second resonant frequency. The further time point within the time period may preferably be selected as desired. Consequently, when the method according to the invention is repeated, a correction may be made to all of the magnetic resonance measurement data captured within the time period. Consequently, the magnetic resonance measurement data can be corrected particularly simply and particularly precisely. If magnetic resonance measurement data that have been corrected in this way are used for a diagnosis and/or evaluation of the examination region of the object undergoing examination, the diagnosis and/or evaluation can be performed particularly precisely and/or reliably. In particular, a result of a medical examination in which the method according to the invention is applied is independent of the magnetic resonance scanner warming up, wherein the cause of the warming may in some cases be independent of the medical examination.

In an embodiment of the method, the magnetic resonance sequence is designed to cause the magnetic resonance measurement data that are acquired at the first time point and/or second time point to be free of modulation caused by phase encoding and/or frequency encoding.

According to this embodiment of the method, the magnetic resonance sequence is designed such that magnetic resonance measurement data is captured at the first time point and/or at the second time point. Gradient switching is applied by the operation of the gradient coil arrangement, with magnetic field gradients being generated thereby. Magnetic field gradients of this kind generate a temporary spatial modulation of the static basic magnetic field and are used for spatially encoding the magnetic resonance measurement data. Magnetic field gradients of this kind generate a spatial modulation, typically a linear modulation, of the phase of the nuclear spins. Typical methods for such spatial encoding are phase encoding and frequency encoding.

Frequency encoding is typically carried out at the same time as the actual acquisition of the magnetic resonance signals, in particular at the same time as connection of an analog/digital converter (ADC) for detecting the magnetic resonance signals. Consequently, the magnetic field gradient that is used for frequency encoding is switched on at the same time as the ADC. A magnetic field gradient of this kind typically generates a linear modulation that is continuous. If a frequency encoding is used for spatial encoding during capture of the magnetic resonance measurement data at the first time point and/or the second time point, then typically said data cannot be free of modulation. According to this embodiment, frequency encoding at the first time point and/or the second time point is preferably omitted. Preferably, the magnetic resonance sequence in this embodiment is designed so that it has no magnetic field gradients for frequency encoding. For example, during spectroscopic measurements a frequency encoding is omitted, wherein instead of frequency encoding in a direction a phase encoding in this direction is performed.

During phase encoding, a magnetic field gradient is switched before certain magnetic resonance signals are actually captured, as a result of which the nuclear spins are modulated during acquisition of the magnetic resonance signals having a position-dependent phase. After the actual capture of the particular magnetic resonance signals, this position-dependent phase is typically neutralized (cancelled) by the switching of an inverse magnetic field gradient. The center of k space is typically captured without switching a magnetic field gradient for phase encoding. If magnetic resonance measurement data are entered in the center of k-space, the data are typically free of modulation as a result of phase encoding. If in addition frequency encoding is omitted, magnetic resonance measurement data that are acquired in this way have no phase that has been changed as a result of the magnetic resonance sequence. Preferably, magnetic resonance measurement data of this kind are acquired at the first time point and/or at the second time point. Based on such magnetic resonance measurement data, the first resonant frequency and/or the second resonant frequency can be determined particularly simply. Such magnetic resonance measurement data reflect magnetic resonance signals that are based on an FID signal or an echo, and a resonant frequency can be extracted from such magnetic resonance signals on the basis of a simple spectroscopic analysis.

Because there is no modulation of the phase of such signals resulting from phase encoding and/or frequency encoding, the resonant frequency can be determined particularly precisely. According to this embodiment, there is no need for correction and/or elimination of any effect of phase encoding and/or frequency encoding, as a result of which the method is particularly robust and precise. If the magnetic resonance sequence is such that it has no frequency encoding, there is no need for an additional module of the magnetic resonance sequence for determining the first resonant frequency and/or for determining the second resonant frequency, as a result of which the time period is not prolonged and the duration of examination of the object undergoing examination can be kept to a minimum.

In an embodiment of the method, the determination of the first resonant frequency is based on magnetic resonance measurement data acquired at the first time point and/or for the determination of the second resonant frequency is based on magnetic resonance measurement data captured at the second time point. The data required for determining the first resonant frequency and/or for determining the second resonant frequency can consequently be captured within the scope of the magnetic resonance sequence. As a result, additional sensors and/or further technical devices can be dispensed with. The resonant frequency may be determined as described above. Preferably, for this purpose magnetic resonance measurement data that are free of phase modulation are used. A method taking this form may be implemented and/or carried out at low cost. Preferably, no additional technical devices are needed, so the method can be implemented flexibly. In particular, the method may thus be combined with different magnetic resonance sequences, including those already used in routine clinical practice. This results in a low-cost and broad range of application of this embodiment of the method.

In another embodiment of the method, magnetic resonance measurement data that are acquired at the first time point and/or second time point are spectroscopic measurement data. The spectroscopic measurement data are preferably spatially resolved. Most spectroscopic images are phase-sensitive, since a temporal change in the phase can be directly reflected in a change in the chemical shifts. If the magnetic resonance measurement data are spectroscopic measurement data, it is accordingly advantageous to correct the magnetic resonance measurement data. If the magnetic resonance measurement data are spectroscopic measurement data and such magnetic resonance measurement data are corrected in accordance with an embodiment of the method according to the invention, then based on the corrected magnetic resonance measurement data a particularly precise evaluation may be performed, for example definition of a spatially resolved chemical shift. In addition, magnetic resonance sequences that are used for spectroscopic images typically are free of frequency encoding, and use phase encoding in at least two spatial directions. Consequently, such magnetic resonance sequences may be combined with the method according to the invention particularly well without increasing the duration of the magnetic resonance sequence.

One embodiment of the method provides for magnetic resonance measurement data that is captured at the first time point and/or second time point to comprise raw image data. Magnetic resonance signals are typically captured in the raw data space and then processed further. If the magnetic resonance measurement data comprises raw image data, it is typically reconstructed to give image data. The image data is then in position space, as a result of which it can be presented particularly clearly. Certain magnetic resonance sequences that are intended to capture raw image data are particularly phase-sensitive. Such phase-sensitive magnetic resonance sequences are based for example on the Dixon method or use a spectral fat saturation. A phase-sensitive magnetic resonance sequence of this kind may also be a single-point sequence, that is to say a magnetic resonance sequence that uses phase encoding in three spatial directions. If phase-sensitive magnetic resonance sequences of this kind are combined with the method according to the invention, the quality of the raw image data and hence the quality of the resulting image data can be improved.

In another embodiment of the method, the magnetic resonance sequence is designed such that, when the magnetic resonance measurement data are acquired, raw data space is scanned at least twice, and the same point in raw data space is filled at the first time point and the second time point. Consequently, the magnetic resonance sequence causes at least one point in the raw data space to be acquired at least twice. When the magnetic resonance measurement data are acquired, typically a number of points in the raw data space are filled with data, wherein at least some of these multiple points are scanned at least twice. A repetition of the acquisition of this kind improves the signal-to-noise ratio, provided the magnetic resonance measurement data are raw image data (i.e. raw data in a form that can be transformed into image data). If the magnetic resonance measurement data are spectroscopic measurement data, then a repetition of this kind can improve the signal-to-noise ratio and/or statistical fluctuations can be compensated particularly well. Consequently, magnetic resonance sequences frequently include such repetitions.

The center of raw data space is scanned (filled with data) in each repetition, since particularly important magnetic resonance measurement data are located in the center of raw data space. It is also possible for other and/or additional points in k-space to be filled in each repetition. Preferably, a point, particularly preferably the center of the raw data space, is scanned in each repetition, with the result that the respective point, preferably the center of raw data space, is scanned at the first time point and at the second time point. In this way, the magnetic resonance sequence is designed such that, in each repetition, as the point of raw data space is scanned, a resonant frequency is determined, based on that point. A time range can be associated with each repetition. The first time the point is captured may be at the first time point, wherein the repetition that includes the first time point is applied by the magnetic resonance sequence in the first time range. The second capture of the point may be at the second time point, wherein the repetition that includes the second time point is applied by the magnetic resonance sequence in the second time range. The resulting first resonant frequency may be used, for example, for correction for the magnetic resonance measurement data captured in the first time range. The resulting second resonant frequency may be used, for example, for correction for the magnetic resonance measurement data captured in the second time range. If the point reflects the center of the raw data space, then the point may be captured free of phase encoding and/or frequency encoding, as a result of which the first resonant frequency and/or the second resonant frequency can be determined particularly precisely. In the case of magnetic resonance sequences that have repetitions and may therefore be of above-average duration, it is particularly advantageous to implement determination of the first resonant frequency and/or the second resonant frequency in this way, since it does not entail a prolongation of the duration of the magnetic resonance sequence. In this way, a duration that is predetermined by the magnetic resonance sequence can be retained in conjunction with the method according to the invention.

Another embodiment of the method provides for the correction to also include the following steps.

The computer determines a further resonant frequency of nuclear spins in the examination region at the further time point, based on the first resonant frequency and the second resonant frequency.

The computer changes the magnetic resonance measurement data that are acquired at the further time point, based on the further resonant frequency.

Preferably, for the correction of magnetic resonance measurement data that are acquired at the further time point within the time period, the further resonant frequency is determined, and the nuclear spins in the examination region precess at that further resonant frequency. If the resonant frequency differs from a reference resonant frequency, which is the first resonant frequency or the second resonant frequency or the carrier frequency, this may bring about a modulation of the magnetic resonance measurement data at the further time point. This modulation may be defined on the basis of the further resonant frequency and a reference resonant frequency. Taking the modulation into account, the magnetic resonance measurement data that are acquired at the further time point may be changed such that the modulation is reduced and/or eliminated. As a result, the influence of the resonant frequency on the magnetic resonance measurement data may be reduced particularly efficiently and/or eliminated particularly precisely.

In another embodiment of the method, for the correction to include determination of a temporally resolved resonant frequency of the magnetic resonance sequence as a function of a time within the time period. Preferably, not only is a further resonant frequency determined for a further time point within the time period, but a temporally resolved resonant frequency that provides for a continuous dependence of the resonant frequency on the time within the time period. Here, preferably the first resonant frequency and the second resonant frequency are used to determine the temporally resolved resonant frequency. Preferably in this case, in addition a model, for example an exponential curve, is used as the basis, such that the temporally resolved resonant frequency can for example be determined iteratively. In this way, for all the magnetic resonance measurement data that are acquired within the time period by the magnetic resonance sequence, the appropriate resonant frequency is determined and/or used for the correction. As a result, correction of the magnetic resonance measurement data can be particularly precise.

Furthermore, the invention encompasses a magnetic resonance apparatus having a control computer and a correction computer. The magnetic resonance apparatus is designed (configured) to perform the method according to the invention for generating corrected magnetic resonance measurement data in an examination region of an object undergoing examination.

For this purpose, the correction computer typically has an input interface, a processor and an output interface. Magnetic resonance measurement data and/or program code for determining the first resonant frequency and/or the second resonant frequency and/or for correcting the magnetic resonance measurement data may be provided to the correction computer via the input interface. Further algorithms, parameters or functions that are needed in the method may be provided to the correction computer via the input interface. The corrected magnetic resonance measurement data and/or further results of embodiments of the method according to the invention may be provided via the output interface. The control computer is configured to apply a magnetic resonance sequence to capture of magnetic resonance measurement data within a time period. The correction computer and/or control computer may be integrated in the magnetic resonance apparatus. The correction computer and/or the control computer may also be installed separately from the magnetic resonance apparatus. The correction computer and/or the control computer may be connected to the magnetic resonance apparatus.

Embodiments of the magnetic resonance apparatus according to the invention are analogous to the embodiments of the method according to the invention described above. The magnetic resonance apparatus may have further control components that are needed and/or advantageous for performing the method according to the invention. The magnetic resonance apparatus may also be configured to emit control signals and/or to receive and/or process control signals in order to perform the method according to the invention. Preferably, the correction computer is part of the control computer of the magnetic resonance apparatus according to the invention. Computer programs and further software may be stored on a memory of the correction computer, and by execution of these programs the processor of the correction computer automatically controls and/or performs the method steps of the method according to the invention.

The present invention also encompasses a non-transitory, computer-readable data storage medium encoded with programming instructions that, when the storage medium is loaded into a computer or a computer system of a magnetic resonance apparatus, cause the computer or computer system in order to implement any or all of the embodiments of the method according to the invention, as described above.

The correction unit must satisfy preconditions, such as having an appropriate RAM, an appropriate graphics card or an appropriate logic unit, so that the respective method steps can be performed efficiently.

Examples of electronically readable data media are a DVD, a magnetic tape or a USB stick on which electronically readable control information, in particular software, is stored.

The advantages of the magnetic resonance apparatus according to the invention and the electronically readable data medium according to the invention correspond substantially to the advantages of the method according to the invention, that were explained in detail above.

DESCRIPTION OF THE PREFERRED EMBODIMENTS

Figure 1:
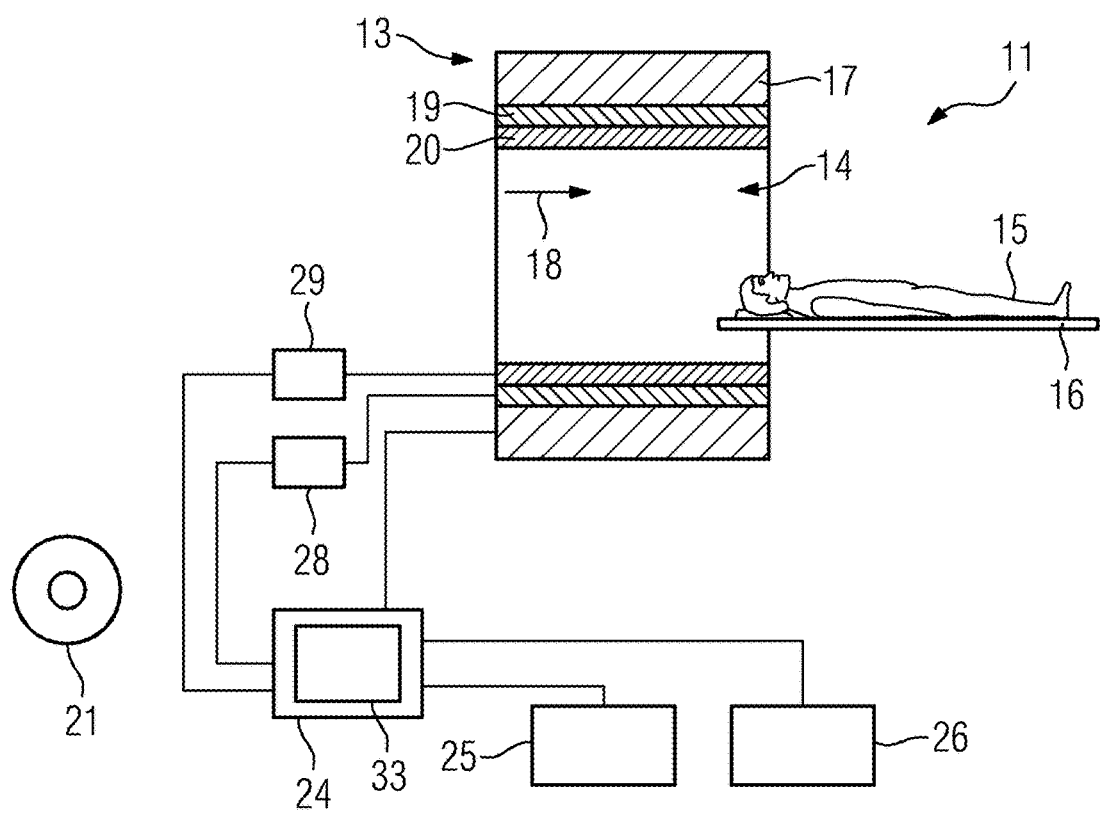
FIG. 1 schematically illustrates a magnetic resonance apparatus according to the invention.

FIG. 1 shows a magnetic resonance apparatus 11 according to the invention for performing the method according to the invention, in a schematic illustration. The magnetic resonance apparatus 11 has a magnetic resonance data acquisition scanner 13, having a basic field magnet 17 for the generation of a strong and constant main magnetic field 18. The scanner 13 has a cylindrical patient-receiving area 14 for receiving a patient 15. The patient-receiving area 14 is peripherally enclosed by the scanner 13. The patient 15 can be moved into the patient-receiving area 14 by a patient support 16. For this purpose, the patient support 16 has a patient table that is movable within the scanner 13.

The scanner 13 further has a gradient coil arrangement 19 for spatially encoding the magnetic resonance signals. The gradient coil arrangement 19 is controlled by a gradient controller 28. Furthermore, the scanner 13 has a radio-frequency antenna 20, which in the case shown is in the form of a body coil that is integrated in fixed manner in the scanner 13, and a radio-frequency antenna controller 29 that operates the radio-frequency antenna unit 20 so as to radiate radio-frequency pulses into an examination volume that is formed substantially by the patient-receiving area 14.

For control of the basic field magnet 17, the gradient controller 28 and the radio-frequency antenna controller 29, the magnetic resonance apparatus 11 has a control computer 24. The control computer 24 exercises central control over the magnetic resonance apparatus 11. Moreover, the control computer 24 includes a reconstruction processor (not illustrated) for the reconstruction of medical image data that are acquired during the magnetic resonance examination. The magnetic resonance apparatus 11 has a display unit 25. Control information, such as control parameters, and reconstructed image data may be displayed on the display unit 25, for example on at least one monitor, for a user. Moreover, the magnetic resonance apparatus 11 has an input unit 26 via which information and/or control parameters can be entered by a user during a measuring procedure. The control computer 24 may include the gradient controller 28 and/or the radio-frequency antenna controller 29 and/or the display unit 25 and/or the input unit 26.

Furthermore, the control computer 24 includes a correction computer 33. The control computer 24, together with the correction computer 33, is configured to perform a method for generating corrected magnetic resonance measurement data in an examination region of an object undergoing examination. The control computer 24 may apply magnetic resonance sequences.

The correction computer 33 has computer programs and/or software that may be loaded directly to a memory (not illustrated) of the correction computer 33, having program code in order to determine a first resonant frequency 51 and a second resonant frequency 52 and to perform a correction of magnetic resonance measurement data based on the first resonant frequency 51 and the second resonant frequency 52 when the computer programs and/or software are executed in the correction computer 33. For this purpose, the correction computer 33 has a processor (not illustrated) that is intended to execute the computer programs and/or software. As an alternative, the computer programs and/or software may also be stored on an electronically readable data medium 21 that is formed separately from the control computer 24 and/or correction computer 33, wherein data access from the correction computer 33 to the electronically readable data medium 21 may be via a data network.

The illustrated magnetic resonance apparatus 11 may include further components that magnetic resonance apparatuses conventionally have. The basic functioning of a magnetic resonance apparatus is known to those skilled in the art, so a more detailed description is not necessary herein. As noted, going beyond such conventional operation, the magnetic resonance apparatus 11, and the control computer 24 and the correction computer 33, are configured to perform the method according to the invention.

The method for generating corrected magnetic resonance measurement data in an examination region of an object undergoing examination may be represented in program code that cause the method to be implemented when the code is executed by the correction computer 33 and/or the correction computer 33. An electronically readable data stored medium 21 has electronically readable control code stored thereon.

Figure 2:
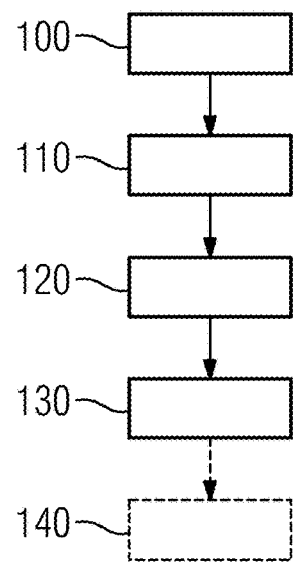
FIG. 2 is a flowchart of an embodiment of the method according to the invention.

FIG. 2 is a flowchart of an embodiment of the method according to the invention for generating corrected magnetic resonance measurement data in an examination region of an object undergoing examination. The method is performed by the control computer 24 and the correction computer 33. At the start of the method, in the method step 100, a magnetic resonance sequence is applied in a time period 40, during which magnetic resonance measurement data are acquired. The magnetic resonance sequence causes magnetic resonance measurement data to be acquired at the first time point and/or second time point so as to be free of modulation resulting from phase encoding and/or frequency encoding.

In the subsequent method step 110, a first resonant frequency 51 is determined at which nuclear spins in the examination region precesses at a first time point 41 within the time period 40. In the method step 120, a second resonant frequency 52 is determined at which nuclear spins in the examination region precesses at a second time point 42 within the time period 40. The method steps 110 and 120 may be performed so as to at least overlap in time. The first resonant frequency 51 may be determined in the method step 110 on the basis of magnetic resonance measurement data acquired at the first time point 41. The second resonant frequency 52 may be determined in the method step 120 on the basis of magnetic resonance measurement data acquired at the second time point 42. The magnetic resonance measurement data acquired at the first time point 41 and/or the second time point 42 may be spectroscopic measurement data. The magnetic resonance measurement data acquired at the first time point 41 and/or the second time point 42 may be raw image data. The magnetic resonance sequence is designed such that when the magnetic resonance measurement data are entered into a memory organized as raw data space at least twice, so the same point in the raw data space is scanned at the first time point 41 and the second time point 42.

In the method step 130, magnetic resonance measurement data that were acquired at a further time point 43 within the time period 40 is corrected on the basis of the first resonant frequency 51 and the second resonant frequency 52. The correction may include the following steps.

A further resonant frequency 53 of nuclear spins in the examination region is determined at the further time point 43, based on the first resonant frequency 51 and the second resonant frequency 52. The magnetic resonance measurement data that are acquired at the further time point 43 are changed, based on the further resonant frequency 53. The correction may also include determining a temporally resolved resonant frequency 55 of the magnetic resonance sequence as a function of a time t within the time period 40.

Optionally, the method step 140 may follow the method step 130, in which case the corrected magnetic resonance measurement data are reconstructed, so as to produce image data, and/or a spectroscopic evaluation of the corrected magnetic resonance measurement data is performed. If the magnetic resonance measurement data are spectroscopic data, then a spectroscopic evaluation of the corrected magnetic resonance measurement data is performed in the method step 140. If the magnetic resonance measurement data are raw image data, then a reconstruction of the corrected magnetic resonance measurement data is performed in the method step 140 in order to produce image data.

Figure 3:
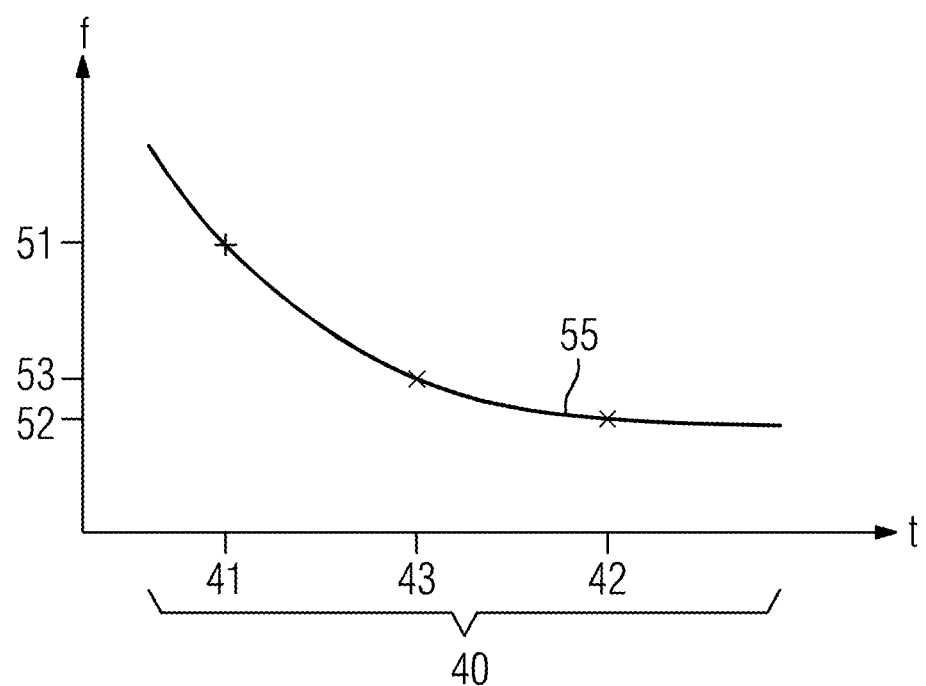
FIG. 3 shows the relationship between a temporally resolved resonant frequency and time.

FIG. 3 shows a graph that illustrates the relationship between a temporally resolved resonant frequency 55 and time t. Here, time t is shown on the horizontal axis, wherein the time t includes the time period 40. A resonant frequency f is shown on the vertical axis. The first resonant frequency 51 at the first time point 41 and the second resonant frequency 52 at the second time point 42 have already been determined, so they are illustrated as functions in the graph in FIG. 3, each marked with a cross. On the basis of the first resonant frequency 51 and the second resonant frequency 52, in the context of correction a further resonant frequency 53 of the magnetic resonance sequence can be determined for a further time point 43. For this purpose, a temporally resolved resonant frequency 55 of the magnetic resonance sequence can be determined as a function of the time t within the time period 40. Typically, the temporally resolved resonant frequency 55 includes the further resonant frequency 53 at the further time point 43.

Furthermore, the correction of the magnetic resonance measurement data may include a change to the magnetic resonance measurement data captured at the further time point 43, on the basis of the further resonant frequency 53. Here, for example a difference between the further resonant frequency 53 and a reference resonant frequency that is for example the first resonant frequency 51 may be formed. On the basis of the difference, a modulation of the magnetic resonance measurement data that was captured at the further time point 43 may be determined. This modulation is taken into account for the correction of the magnetic resonance measurement data captured at the further time point 43.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for generating corrected magnetic resonance (MR) measurement data in an examination region of an examination object, comprising:
    operating an MR data acquisition scanner, while an examination object is situated therein, in order to acquire MR measurement data, from an examination region of the examination subject, within a time period;
    in a computer, determining a first resonant frequency of nuclear spins in the examination region at a first time point within the time period;
    in said computer, determining a second resonant frequency of nuclear spins in the examination region at a second time point within the time period;
    operating the MR data acquisition scanner in order to acquire further MR measurement data from the examination region of the examination object at a further time point within the time period;
    in said computer, correcting the MR measurement data acquired at said further time point, based on the first resonant frequency and the second resonant frequency, and thereby producing corrected MR measurement data;
    making the corrected MR measurement data available from the computer in electronic form as an output from said computer; and
    operating said MR data acquisition scanner by executing an MR data acquisition sequence that causes the MR measurement data to be entered into a memory, organized as raw data space, at least twice, with a same point in raw data space being scanned at said first time point and said second time point.

2. A method as claimed in claim 1, wherein, said MR data acquisition scanner is operated within the time period to acquire said MR measurement data at at least one of said first time point and said second time point so as to be free of modulation caused by encoding selected from the group consisting of phase encoding and frequency encoding.

3. A method as claimed in claim 1, wherein said MR data acquisition scanner is operated within the time period to acquire said MR measurement data at said first time point, and further comprising determining said first resonant frequency based on the MR measurement data acquired at said first time point.

4. A method as claimed in claim 1, wherein said MR data acquisition scanner is operated within the time period to acquire said MR measurement data at said second time point, and further comprising determining said second resonant frequency based on said MR measurement data acquired at said second time point.

5. A method as claimed in claim 1, wherein said MR data acquisition scanner is operated within the time period to acquire said MR measurement data at at least one of said first time point and said second time point to acquire said MR measurement data at at least one of said first time point and said second time point as spectroscopic measurement data.

6. A method as claimed in claim 1, wherein said MR data acquisition scanner is operated within the time period to acquire said MR measurement data at at least one of said first time point and said second time point to acquire said MR measurement data at at least one of said first time point and said second time point as raw image data.

7. A method as claimed in claim 1 comprising producing said corrected MR measurement data in said computer by:
    determining a further resonant frequency of said nuclear spins in said examination region at said further time point, based on said first resonant frequency and said second resonant frequency; and
    changing said MR measurement data acquired at said further time point based on said further resonant frequency.

8. A method as claimed in claim 1 comprising producing said corrected MR data by determining a temporally resolved resonant frequency of the MR measurement data as a function of time within said time period.

9. A magnetic resonance (MR) apparatus comprising:
    an MR data acquisition scanner;
    a computer configured to operate said MR data acquisition scanner, while an examination object is situated therein, in order to acquire MR measurement data, from an examination region of the examination subject, within a time period;
    said computer being configured to determine a first resonant frequency of nuclear spins in the examination region at a first time point within the time period;
    said computer being configured to determine a second resonant frequency of nuclear spins in the examination region at a second time point within the time period;

said computer being configured to operate the MR data acquisition scanner in order to acquire further MR measurement data from the examination region of the examination object at a further time point within the time period;

said computer being configured to correct the MR measurement data acquired at said further time point, based on the first resonant frequency and the second resonant frequency, and thereby producing corrected MR measurement data;

said computer being configured to make the corrected MR measurement data available from the computer in electronic form as an output from said computer; and said computer being configured to operate said MR data acquisition scanner by executing an MR data acquisition sequence that causes the MR measurement data to be entered into a memory, organized as raw data space, at least twice, with a same point in raw data space being scanned at said first time point and said second time point.

10. A non-transitory, computer-readable data storage medium encoded with programming instructions, said storage medium being loaded into at least one computer of a magnetic resonance (MR) apparatus that comprises an MR data acquisition scanner, said programming instructions causing said at least one computer to:

operate said MR data acquisition scanner, while an examination object is situated therein, in order to acquire MR measurement data, from an examination region of the examination subject, within a time period;

determine a first resonant frequency of nuclear spins in the examination region at a first time point within the time period;

determine a second resonant frequency of nuclear spins in the examination region at a second time point within the time period;

operate the MR data acquisition scanner in order to acquire further MR measurement data from the examination region of the examination object at a further time point within the time period;

correct the MR measurement data acquired at said further time point, based on the first resonant frequency and the second resonant frequency, and thereby producing corrected MR measurement data;

make the corrected MR measurement data available from the computer in electronic form as an output from said at least one computer; and operate said MR data acquisition scanner by executing an MR data acquisition sequence that causes the MR measurement data to be entered into a memory, organized as raw data space, at least twice, with a same point in raw data space being scanned at said first time point and said second time point.

11. A method for generating corrected magnetic resonance (MR) measurement data in an examination region of an examination object, comprising:

operating an MR data acquisition scanner, while an examination object is situated therein, in order to acquire MR measurement data, from an examination region of the examination subject, within a time period;

in a computer, determining a first resonant frequency of nuclear spins in the examination region at a first time point within the time period;

in said computer, determining a second resonant frequency of nuclear spins in the examination region at a second time point within the time period;

operating the MR data acquisition scanner in order to acquire further MR measurement data from the examination region of the examination object at a further time point within the time period;

in said computer, correcting the MR measurement data acquired at said further time point, based on the first resonant frequency and the second resonant frequency, and thereby producing corrected MR measurement data; and making the corrected MR measurement data available from the computer in electronic form as an output from said computer, wherein the act of producing said corrected MR measurement data in said computer includes:

determining a further resonant frequency of said nuclear spins in said examination region at said further time point, based on said first resonant frequency and said second resonant frequency; and changing said MR measurement data acquired at said further time point based on said further resonant frequency.

12. A method as claimed in claim 11, wherein, said MR data acquisition scanner is operated within the time period to acquire said MR measurement data at at least one of said first time point and said second time point so as to be free of modulation caused by encoding selected from the group consisting of phase encoding and frequency encoding.

13. A method as claimed in claim 11, wherein said MR data acquisition scanner is operated within the time period to acquire said MR measurement data at said first time point, and further comprising determining said first resonant frequency based on the MR measurement data acquired at said first time point.

14. A method as claimed in claim 11, wherein said MR data acquisition scanner is operated within the time period to acquire said MR measurement data at said second time point, and further comprising determining said second resonant frequency based on said MR measurement data acquired at said second time point.

15. A method as claimed in claim 11, wherein said MR data acquisition scanner is operated within the time period to acquire said MR measurement data at at least one of said first time point and said second time point to acquire said MR measurement data at at least one of said first time point and said second time point as spectroscopic measurement data.

16. A method as claimed in claim 11, wherein said MR data acquisition scanner is operated within the time period to acquire said MR measurement data at at least one of said first time point and said second time point to acquire said MR measurement data at at least one of said first time point and said second time point as raw image data.

17. A method as claimed in claim 11, comprising operating said MR data acquisition scanner by executing an MR data acquisition sequence that causes the MR measurement data to be entered into a memory, organized as raw data space, at least twice, with a same point in raw data space being scanned at said first time point and said second time point.

18. A method as claimed in claim 11, comprising producing said corrected MR data by determining a temporally resolved resonant frequency of the MR measurement data as a function of time within said time period.

* * * * *